United States Patent
Khairoun et al.

(10) Patent No.: US 7,351,280 B2
(45) Date of Patent: Apr. 1, 2008

(54) MACROPOROUS, RESORBABLE AND INJECTIBLE CALCIUM PHOSPHATE-BASED CEMENTS (MCPC) FOR BONE REPAIR, AUGMENTATION, REGENERATION, AND OSTEOPOROSIS TREATMENT

(75) Inventors: Ibrahim Khairoun, Nantes (FR);
Racquel Z. LeGeros, New York, NY (US); Guy Daculsi, Bretagne (FR);
Jean-Michael Bouler, Nantes (FR);
Jérôme Guicheux, Nantes (FR);
Olivier Gauthier, Sucé-sur-Erdre (FR)

(73) Assignees: New York University, New York, NY (US); Institut National Dela Sante ET Dela Recherche Medicale, Paris Cedex (FR); The University of Nantes, Nantes Cedex (FR)

( * ) Notice: Subject to any disclaimer, the term of this patent is extended or adjusted under 35 U.S.C. 154(b) by 317 days.

(21) Appl. No.: 11/054,623

(22) Filed: Feb. 9, 2005

(65) Prior Publication Data
US 2005/0199156 A1 Sep. 15, 2005

Related U.S. Application Data

(60) Provisional application No. 60/543,230, filed on Feb. 10, 2004.

(51) Int. Cl.
*C04B 12/02* (2006.01)

(52) U.S. Cl. .......... 106/690; 106/691; 106/35; 623/23.62

(58) Field of Classification Search .......... 106/35, 106/690, 691; 623/23.62; 424/603, 602
See application file for complete search history.

(56) References Cited

U.S. PATENT DOCUMENTS

| | | | |
|---|---|---|---|
| 5,525,148 A | 6/1996 | Chow et al. |
| 5,650,176 A | 7/1997 | Lee et al. |
| 5,683,461 A | 11/1997 | Lee et al. |
| 5,820,632 A | 10/1998 | Constantz et al. |

*Primary Examiner*—C. Melissa Koslow
(74) *Attorney, Agent, or Firm*—Klauber & Jackson

(57) ABSTRACT

A composition and method for producing interconnective macroporous, resorbable and injectable calcium phosphate-based cements (MICPCs). The composition of the invention sets to poorly crystalline apatitic calcium phosphate after mixing a powder component and an aqueous solution. The multiphasic calcium phosphate components in the cement resorb at different rates allowing the timely replacement by new bone. The interconnected macroporosity in the cement allows for vascularization, entrapment of growth factors, cell colonization and tissue ingrowth. This MICPC can be used for dental and medical applications relating to bone repair, augmentation, reconstruction, regeneration, and osteoporosis treatment, and also for drug delivery, and as scaffolds for tissue engineering.

19 Claims, 7 Drawing Sheets

First porosity after 24 hours setting of the cement composed of 45% α-TCP, 15% ACCP-F, 30% BCP granules (40-200 microns), 5% MCP and 5% CC, L/P = 0.40ml/g and the liquid 3% Na2HPO4/NaH2PO4 in water and a pH of 6.5.

FIG 1. (a) X-ray diffraction pattern of an amorphous calcium phosphate (ACCP-Mg). (b) FTIR spectra of an amorphous calcium phosphate (ACCP-Mg).

Fig 2. First porosity after 24 hours setting of the cement composed of 45% α-TCP, 15% ACCP-F, 30% BCP granules (40-200 microns), 5% MCP and 5% CC, L/P = 0.40ml/g and the liquid 3% Na2HPO4/NaH2PO4 in water and a pH of 6.5.

Fig 3. (A) The poorly crystalline aspect of the product of the reaction after 3 days setting. (B) Cement prepared with 100% alpha-TCP.

Fig 4. (a) XRD of the cement (α-TCP, 45%; ACCP-Mg, 15%; BCP.30%; MCPA, 5%; CC, 5%; Liquid: 3% Na2HPO4 / NaH2PO4, pH 6.5, L/P = 0.40 ml/g, 24 hours after setting. (b) FTIR of cement 48 hrs after setting.

SEM pictures illustrating the cell morphology and spreading on different cement samples

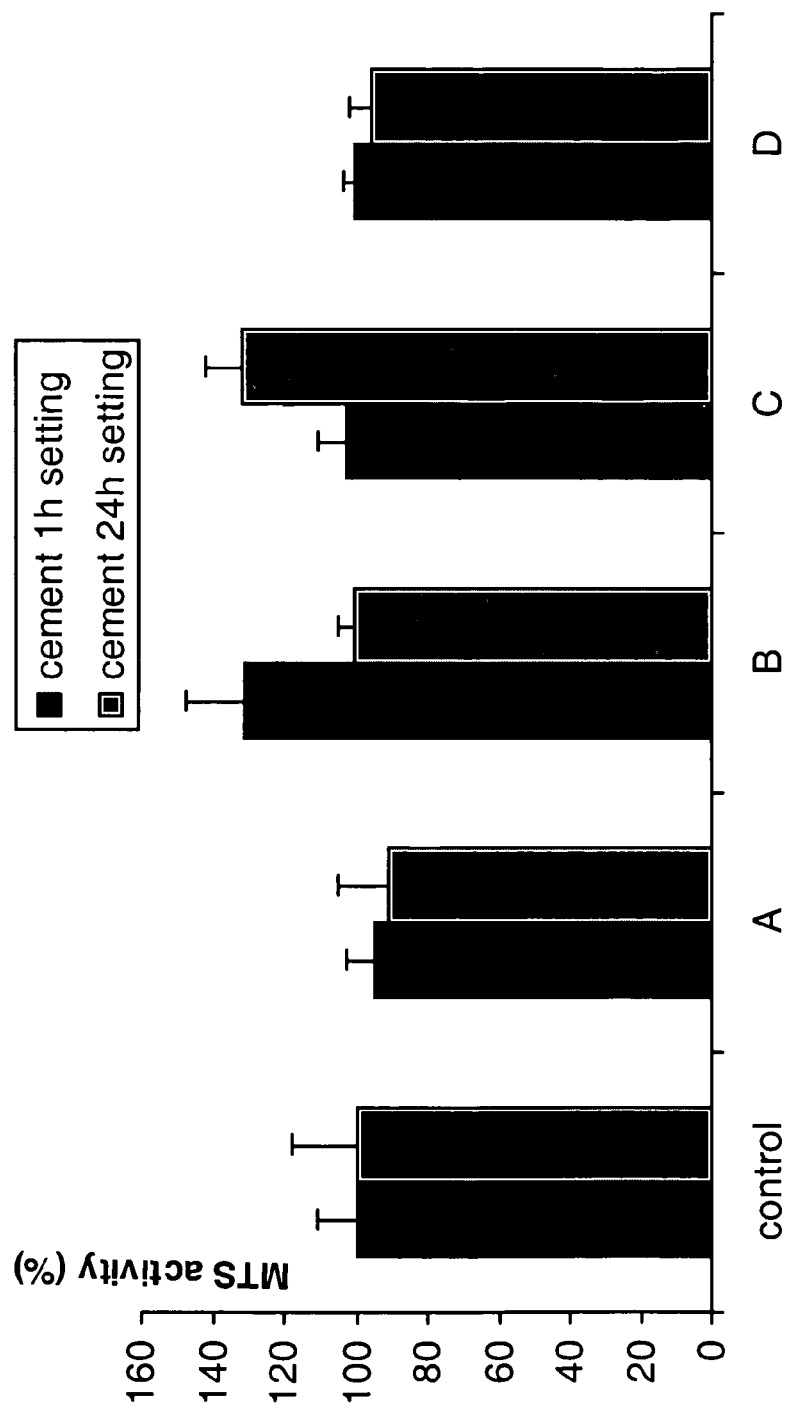
Fig 6. Cell viability after 15 days culture on different cement formulations

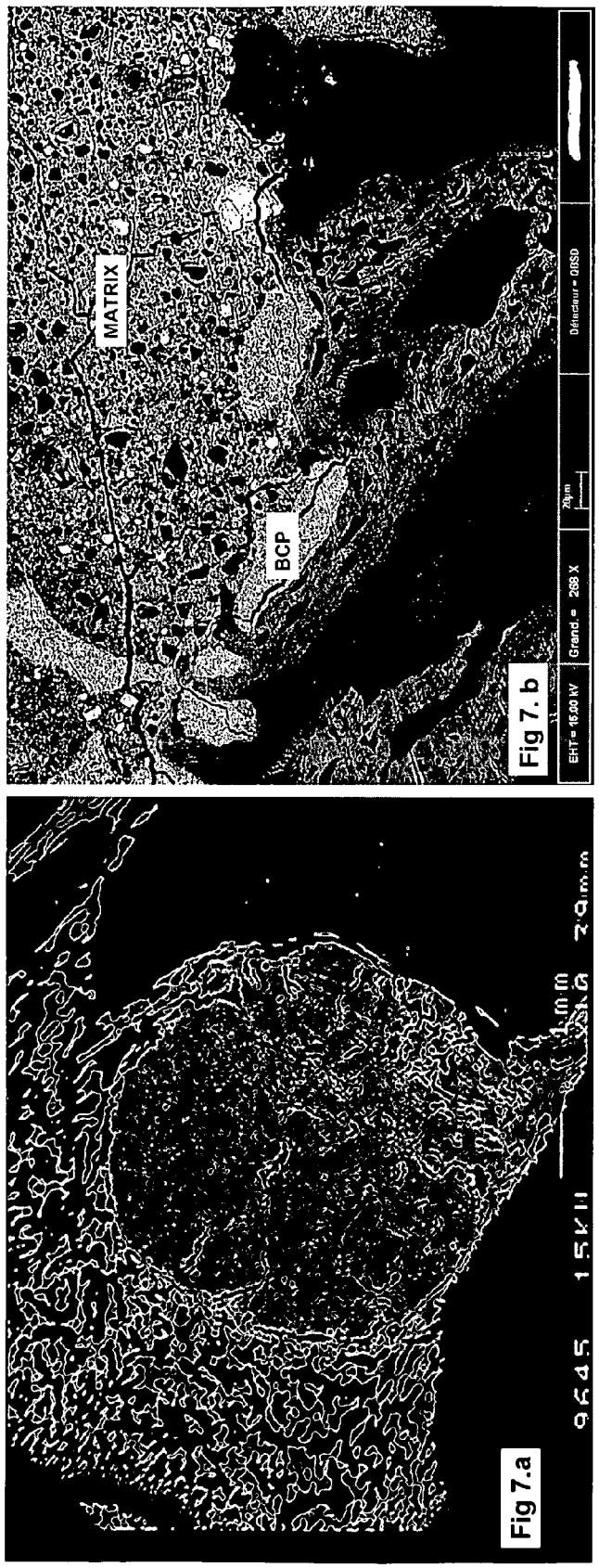
Fig 7. (a) SEM micrograph of the defect after 3 weeks of implantation of a typical calcium phosphate preparation (CPC) containing mainly α-TCP. (b) SEM picture illustrating the open structure of our macroporous injectable calcium phosphate cement MICPC (containing ACP and BCP) after 3 weeks implantation in rat femora.

MACROPOROUS, RESORBABLE AND INJECTIBLE CALCIUM PHOSPHATE-BASED CEMENTS (MCPC) FOR BONE REPAIR, AUGMENTATION, REGENERATION, AND OSTEOPOROSIS TREATMENT

RELATED APPLICATION

This application claims priority from U.S. Provisional Patent Application 60/543,230, filed Feb. 10, 2004.

FIELD OF INVENTION

This invention relates generally to methods and compositions for bone repair, augmentation and regeneration, and to osteoporosis treatment. More specifically the invention relates to preparation of and uses for an interconnective macroporous, resorbable and injectible calcium phosphate-based cement.

BACKGROUND OF INVENTION

Bone is a composite of biopolymers (principally collagen), and an inorganic component identified as carbonate hydroxyapatite, approximated as $(Ca,Mg,Na,M)_{10}(PO_4,CO_3,HPO_4)_6(OH,Cl)_2$ [See LeGeros R Z (1981). "Apatites in Biological Systems". *Prog Crystal Growth* 4: 1-45; and LeGeros R. Z. (1991). *Calcium Phosphates in Oral Biology and Medicine*. Monographs in Oral Sciences. Vol 15. Myers H. M. (ed). Karger, Basel].

Calcium phosphate materials, principally hydroxyapatite (HA), beta-tricalcium phosphate (β-TCP), biphasic calcium phosphates, BCP (consisting of a mixture of HA and β-TCP in varying HA/β-TCP ratios) are commercially available as biomaterials for bone repair, augmentation or substitution. The principal advantages of calcium phosphate materials are: similarity in composition to the bone mineral, bioactivity, osteoconductivity and ability to form a uniquely strong interface with bone. Calcium phosphate materials are available as granules, blocks, coatings on dental and medical implants, and as cements.

Calcium phosphate cements (CPCs). The concept and potential advantages of an apatitic or calcium phosphate cement (CPC) as a possible restorative material was first introduced by LeGeros et al in 1982. [See LeGeros R. Z., Chohayeb A, Shulman A (1982). "Apatitic Calcium Phosphates: Possible Restorative Materials." *J Dent Res* 61(Spec Iss):343]. This early formulation was based on mixing calcium-deficient or precipitated apatite (CDA) and calcium hydroxide with phosphoric acid. In 1987, Brown and Chow reported the first hardening CPC resulting from mixing tetracalcium phosphate (TTCP) and dicalcium phosphate anhydrous (DCPA). There are presently numerous patents on CPC and several CPC commercial products. Compared to calcium phosphates that are available in particulate or block forms, CPC has the following desirable properties and decided advantages: malleability (allowing it to adapt to the site and shape of the defect and high bioresorbability (allowing it to be replaced by bone). The introduction of injectable calcium phosphate cements greatly improved the handling and delivery of the cements and opened up areas of new applications for the CPC. [Niwa S., LeGeros R. Z. (2002). Injectable Calcium Phosphate Cements for Repair of Bone Defects, In: Lewandrowski, K. A., Wise D. L., Taratola D. (eds). *Tissue Engineering and Biodegradable Equivalents: Scientific and Clinical Applications*. New York, Marcel Dekker, Inc. pp. 385-399.]

Calcium phosphate cement (CPC) systems consist of a powder and a liquid component. The powder component is usually made up of one or more calcium phosphate compounds with or without additional calcium salts. Other additives are included in small amounts to adjust the setting times, increase injectability, reduce cohesion or swelling time, and/or introduce macroporosity. Current commercial CPCs include two or more of the following calcium phosphate compounds: amorphous calcium phosphate (ACP), $Ca_x(PO_4)_y.H_2O$; monocalcium phosphate monohydrate (MCPH), $CaH_4(PO_4)_2.H_2O$; dicalcium phosphate dihydrate (DCPD), $CaHPO_4.2H_2O$; dicalcium phosphate anhydrous (DCPA), $CaHPO_4$; precipitated or calcium-deficient apatite (CDA), $(Ca,Na)_{10}(PO_4,HPO_4)_6(OH)_2$; alpha- or beta-tricalcium phosphate (α-TCP, β-TCP), $Ca_3(PO_4)_2$; and tetracalcium phosphate (TTCP), $Ca_4P_2O_9$. Other calcium salts include: calcium carbonate (CC), calcium oxide or calcium hydroxide (CH), calcium sulfate hemihydrate (CSH), and calcium silicate. The liquid component may be one or combinations of the following solutions: saline, deionized $H_2O$, dilute phosphoric acid, dilute organic acids (acetic, citric, succinic), sodium phosphate (alkaline or neutral), sodium carbonate or bicarbonate, sodium alginate, sodium bicarbonate, and/or sodium chondroitin sulfate. The setting reaction product(s) obtained after the cement has set is (are) determined by the composition of the powder component and composition and the pH of the liquid component. The setting time (which can range from 10 to 60 min) is determined by the composition of the powder and liquid components, the powder-to-liquid ratio (P/L), proportion of the calcium phosphate components (e.g., TTCP/DCPA ratio) and the particle sizes of the powder components. Apatitic calcium phosphate or carbonate-containing apatite (carbonatehydroxyapatite, CHA) with crystallinity (crystal size) similar to that of bone apatite can form before implantation when the cement sets or can result from the in vivo hydrolysis of the non-apatitic setting product (e.g., DCPD) after implantation.

The currently available commercial CPCs set as a dense mass and therefore suffer from some shortcomings such as absence of interconnecting macroporosity and slow rate of bioresorbability. Appropriate macroporosity (100-300μ) in the cement is critical to allow for vascularization and tissue ingrowth to take place and thus facilitate the formation of new bone. In addition, appropriate porosity allows the incorporation of drugs and therapeutic agents (e.g, antibiotics, antiresorption agents for osteoporosis; anticancer agents, etc) or growth factors (e.g., bone morphogenetic proteins; BMPs and other bioactive molecules). Appropriate rate of bioresorbability is critical for the timely replacement of the cement with new bone.

Several methods of introducing macroporosity in the CPC have been recommended. These methods include: introduction of resorbable fibers, e.g., polygalactin; addition of soluble salts (e.g. calcium chloride and sodium or potassium hydroxide; addition of pore forming agents (e.g., sugar, $NaHCO_3$, calcium salts); using frozen sodium phosphate ($Na_2HPO_4$) solution particles; adding acidic sodium phosphate ($NaH_2PO_4$) solution to $NaHCO_3$; and providing acid (citric acid) and base ($NaHCO_3$). These methods produce macroporosity from the liberation of $CO_2$ during the reaction of acid and $NaHCO_3$.

SUMMARY OF INVENTION

The macroporous, bioresorbable and injectable calcium phosphate cement (MICPC) of the present invention provides macroporosity and resorbability not exhibited by currently available CPC. Features of the invention include: (1) incorporation of biphasic calcium phosphate (BCP) and amorphous calcium phosphate (ACP) as principal compounds in the powder component and (2) providing macroporosity of the cement. These combined features are not present in the calcium phosphate cements presently available.

Biphasic calcium phosphate, BCP, is currently used in many medical and dental applications. Because it consists of an intimate mixture of HA and β-TCP and because of the difference in their solubility (β-TCP >>>HA), bioresorbability or bioactivity can be controlled by manipulating the HA/β-TCP ratio of the BCP. [LeGeros R Z and Daculsi G (1990). In vivo transformation of biphasic calcium phosphate ceramics: ultrastructural and physico-chemical characterizations. In: *Handbook of Bioactive Ceramics*. Vol II. Calcium Phosphate Ceramics. Yamamuro N, Hench L, Wilson-Hench J (eds), CRC Press, Boca Raton, pp. 17-28]. The HA/β-TCP (e.g., 60/40, 20/80, etc) ratio in the BCP can be easily controlled by controlling the synthesis parameters.

Amorphous calcium phosphate, ACP, is used as a major component of a commercial CPC. ACP is the most soluble in the group of calcium phosphate compounds used in many CPCs. ACP can be made more or less stable (i.e., more or less soluble or more or less susceptible to transforming to other calcium phosphates) depending on the ions incorporated in it. [LeGeros R Z et al, (1973). Amorphous calcium phosphates: synthetic and biological. *Colloque Internationaux CNRS No.* 230, "Physico-chimie et Cristallogrpahie des Apatites d'Interet Biologique", Paris, pp 105-115].

The cement of the invention contains four calcium phosphate compounds with BCP, ACP (modified or unmodified composition) and α-TCP or TTCP as the principal components. These calcium phosphates differ in their solubilities and therefore in their rate of resorbability: ACP>>α-TCP>>BCP and in BCP, β-TCP>>HA [LeGeros R Z (1993) Biodegradation/bioresorption of calcium phosphate materials. *Clin Mat* 14:65-88]. In vivo, the preferential dissolution of ACP and the difference in the rates of dissolution of the other calcium phosphate compounds provide internal interconnecting macroporosity in the cement allowing for vascularization, entrapment of growth factors, cell colonization and tissue ingrowth. The addition of minor quantities of acidic and basic compounds allows the formation of macroporosity as the components of the cement are mixed and as the cement sets. Thus, this invention provides macroporous, injectable calcium phosphate cements ("MICPCs") with programmable bioresorbability and interconnecting macroporosity.

This MICPC can be used for dental and medical applications relating to bone repair, augmentation, reconstruction, regeneration, and osteoporosis treatment, and also for drug delivery, and as scaffolds for tissue engineering. Other potential dental applications are: repair of periodontal defects, sinus augmentation, maxillofacial reconstruction, pulp-capping materials, cleft-palate repair, and as adjuvants to dental implants. Additional medical applications include repair of large bony defects, repair of bone fractures cause by trauma, or associated with osteoporosis; for spine fusion, surgery revision, bone augmentation, and for bone reconstructions associated with cancer therapy.

DESCRIPTION OF DRAWINGS

In the drawings appended hereto:

FIG. 6 depicts cell viability after 15 days culture for different cement formulations;

FIG. 7a is an SEM micrograph of the defect after 3 weeks of implantation of a typical calcium phosphate preparation (CPC) containing mainly α-TCP; and FIG. 7b is a SEM micrograph illustrating the open structure of a macroporous injectable calcium phosphate cement MICPC in accordance with the invention (containing ACP and BCP), after 3 weeks implantation in rat femora.

DESCRIPTION OF PREFERRED EMBODIMENTS

Figure 1:
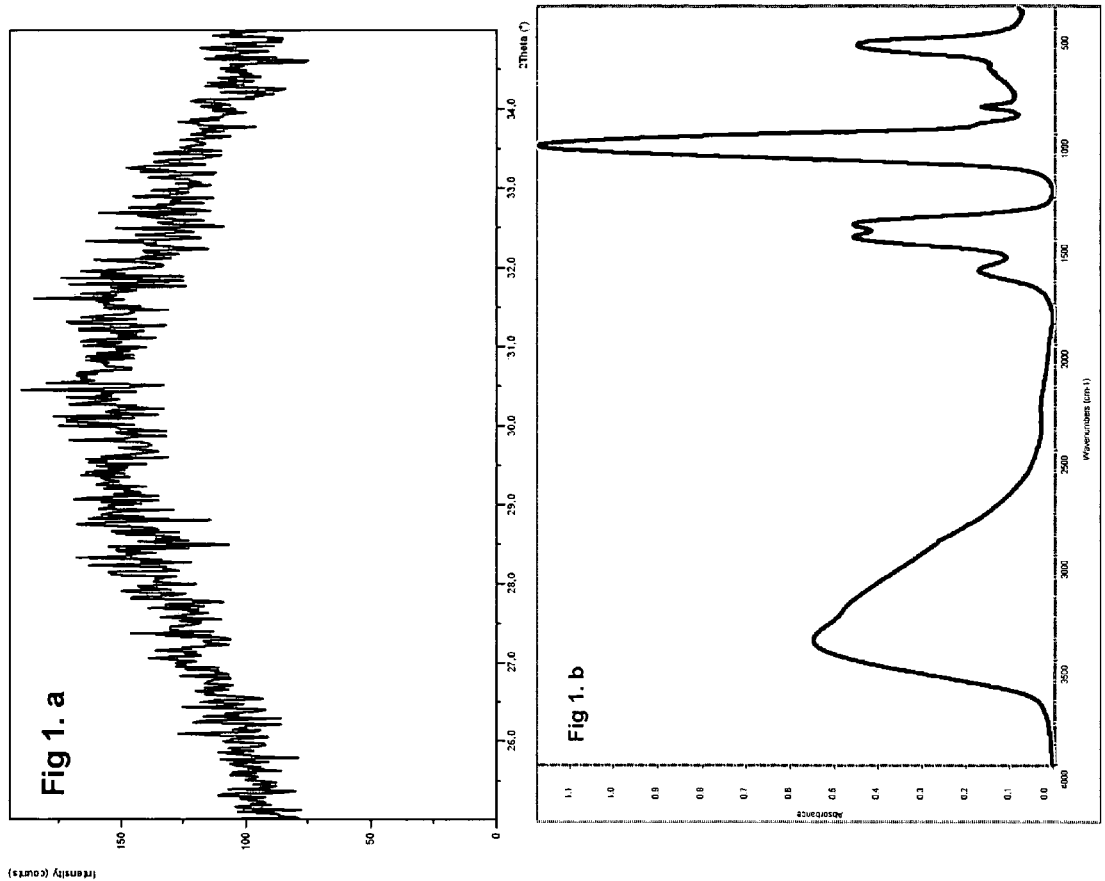
FIG. 1a shows the typical x-ray diffraction pattern of an amorphous calcium phosphate characterized by a high background and absence of any diffraction peaks.
FIG. 1b shows an infrared (FTIR) spectrum of the freeze-dried amorphous calcium carbonate phosphate (ACCP) preparation.

The present invention provides a method of preparing injectable and bioresorbable calcium phosphate cement (CPC) compositions, which self-harden to form poorly crystalline hydroxyapatite at room or body temperatures when in contact with an aqueous solution, combining one or more sparingly soluble calcium phosphates along with an acid and base to produce a self-setting cement with interconnected porosity.

In accordance with the invention, the major fraction of the powder component consists of the following principal calcium phosphate compounds: α-TCP or TTCP, BCP, and ACP. In some embodiments, the α-TCP or TTCP, BCP, and ACP are present in decreasing percentages, respectively. The α-TCP or TTCP particles typically have a median particle size of about 7 microns. The macroporous BCP granules (consisting of an intimate mixture of HA and β-TCP in varying HA/β-TCP ratios) have a typical particle size between about 40 and 600 microns, preferably between about 200 and 500 microns. The ACP can be non-stabilized (only calcium and phosphate) or stabilized (s-ACP), or a mixture of both. The stabilizing ion may be zinc (Zn-ACP), magnesium (Mg-ACP) pyrophosphate (P2-ACP) or carbonate (ACCP) or a combination of ions [LeGeros R Z (1991) "Calcium Phosphates in Oral Biology and Medicine". Monographs in Oral Sciences. Vol 15, Myers H. M. (ed) Karger, Basel]. The minor fraction and components of the powder mixture comprises monocalcium phosphate monohydrate (MCPM)] or monocalcium phosphate (MCP) or calcium carbonate (CC) or amorphous calcium carbonate phosphate (ACCP). This minor fraction can also be a mixture of two, three or four of the compounds.

The liquid component used with the powders consists of an aqueous solution with a pH ranging from about 5 to 10. This liquid component is prepared by dissolving in aqueous solution appropriate amounts of $Na_2HPO_4$ or $K_2HPO_4$ or $NaH_2PO4$ or $KH_2PO_4$ or a mixture thereof. In order to obtain a poorly crystalline apatite upon setting before or after implantation, the pH of the liquid component should preferably be between 5 and 7. Other additives may be also added to the liquid component.

The powder component thus comprises calcium phosphate salts with differing dissolution rates. The combination of the matrix (which may includes α-TCP or TTCP, ACP, MCP, MCP, CC, ACCP) and the macroporous BCP granules, can overcome the uncontrolled resorption exhibited by other cements, and allows the timely replacement of the cement by forming new bone.

The percentage (w/w/) of the combination of the calcium phosphate compounds excluding BCP is from about 10% to 70% based on the total dry weight of the powder phase. In some embodiments, the majority of the weight of the calcium phosphate compounds is provided by α-tricalcium phosphate, in other embodiments, the majority of the weight of the calcium phosphate compounds is provided by tetracalcium phosphate, and in still other embodiments, the majority of the weight of the calcium phosphate compounds comprises α-tricalcium phosphate and/or tetracalcium phosphate.

The content (% w/w) of the unstabilized or stabilized amorphous calcium phosphate, is from about 5% to 30% based on the total dry weight of the powder phase.

The content (% w/w) of the macroporous BCP granules is from about 10% to 70% based on the total dry weight of the powder phase. In preferred embodiments, the w/w ratio of the BCP granules to the remaining calcium phosphate compounds is selected such that the final result of their combination does not change the final pH of the mixture of the powder and liciuid components.

The content (% w/w) of the minor fraction is from about 1% to 10% based on the total dry weight of the powder phase.

The present invention may further control the consistency and increase the injectability of the cement paste resulting from mixing the powder and the liquid by dissolving biodegradable oligomers and polymers into the liquid phase prior to mixing the powder and liquid components. The biodegradable polymers may be selected from the group of hyaluronic acid, hyaluronate salts, hydroxypropylmethyl cellulose, dextran, alginate, chitosan, agarose, polyethylene glycols (PEG), polyhydroxyethylenemethacrylats (HEMA), synthetic and natural proteins, or collagen. The dissolution of the polymers in the resulting paste of the calcium phosphate cement will improve injectability of the calcium phosphate cement paste.

The main calcium phosphate compounds may be combined with other additives such as calcium sulfate hemihydrate or calcium sulphate dihydrate or a combination of both that can be used to regulate the setting time or to act as pore-forming agents due to their fast dissolution.

Additionally, the cement may incorporate pharmaceutically active ingredients or biologically and physiologically active substances that have a wide range of applications, preferably selected from the group of antibiotics, anti-inflammatory drugs, anti-cancer drugs, peptides, and proteins such as growth factors. The growth factors can be such as BMP (Bone Morphogenetic Protein), FGF (Fibroblast Growth Factor). The antibiotic is preferably a gentamicin or a gentamicin salt, typically gentamicin sulfate. Owing to their structure and their dissolution property, the calcium phosphate cements are able to slowly release the active ingredients into the environment within a few days after implantation.

EXAMPLE 1

Preparation of Amorphous Calcium Phosphate (ACP) and Modified ACP at 25° C.

(i) Amorphous Calcium Phosphate: ACP.

Reagents: $Na_2HPO_4 \cdot 2H_2O$ (0.25 mol/l); $CaCl_2 \cdot 2H_2O$ (0.75 mol/l). (These concentrations gave a final phosphate concentration of 0.15 mol/l and a Ca/P molar ratio of 1.71).

The calcium solution was added rapidly with stirring to the phosphate solution. All solutions were adjusted to pH 10 with concentrated NaOH prior to mixing. The initial solid phase formed immediately on mixing was filtered, washed (with distilled water+NaOH, pH 10), and then freeze-dried.

(ii) Amorphous Calcium Phosphate Containing Carbonate: ACCP.

Reagents: $Na_2HPO_4 \cdot 2H_2O$ (0.25M), $NaHCO_3$ (0.25M), $CaCl_2 \cdot 2H_2O$ (0.75 M). solution molar ratio of $CO_3/P=5/1$.

The calcium and (phosphate+carbonate) solutions were first adjusted to pH 10 using $NH_4OH$. 100 ml of the calcium solution was quickly added to the stirring phosphate and carbonate solution (100 ml). Precipitate was filtered, washed (with distilled water+NaOH, pH 10), then freeze dried.

(iii) Amorphous Calcium Carbonate Phosphate Containing Fluoride: ACCP-F

Reagents: $Na_2HPO_4 \cdot 2H_2O+NaHCO_3+NaF$ (0.25M); $CaCl2 \cdot 2H_2O$ (0.75 M) ($CO_3/P=5/1$; $F/P=0.1/1$ molar ratio)

(iv) Amorphous Calcium Carbonate Phosphate Containing Magnesium: ACCP-Mg.

Reagents: $Na_2HPO_4 \cdot 2H_2O+NaHCO_3$ $(0.25M)$; $CaCl_2 \cdot 2H_2O+Mg(Cl)_2, 6H_2O$ (0.75M)

($CO_3/P$ 5/1; Mg/Ca 0.2/1 molar ratio)

(v) Amorphous Calcium Carbonate Phosphate Containing Zinc: ACCP-Zn

Reagents: $Na_2HPO_4 \cdot 2H_2O+NaHCO_3$ $(0.25M)$; $CaCl_2 \cdot 2H_2O+Zn(Cl)_2, 6H_2O$ (0.75M)

($CO_3/P$ 5/1; Zn/Ca 0.03/1 molar ratio)

Characterization of the amorphous calcium phosphate preparations: FIG. 1a shows the typical x-ray diffraction pattern of an amorphous calcium phosphate characterized by a high background and absence of any diffraction peaks. FIG. 1b shows an infrared (FTIR) spectrum of the freeze-dried amorphous calcium carbonate phosphate (ACCP) preparation. FTIR absorption bands for $CO_3$ groups (at 1420 to 1450 $cm^{-1}$; 970 to 980 $cm^{-1}$) and for $PO_4$ groups (at 950 to 1200 $cm^{-1}$ and 450 to 650 $cm^{-1}$) are present. The lack of resolution of the $PO_4$ absorption bands is typical characteristics of ACCP.

EXAMPLE 2

Preparation of a Calcium Phosphate Cement Formulation

Cement samples with different liquid-to-powder ratio were prepared. For one formulation, the powder of the cement contained 45% α-TCP, 15% ACCP, 30% BCP macroporous granules (40-200μ), 5% MCPA and 5% CC. The HA/β-TCP of the BCP was 60/40. The liquid/powder ratio L/P of the cements varied from 0.30 or 0.32 or 0.35 or 0.40 ml/g. The liquid concentration was 3% $Na_2HPO_4$/$NaH_2PO_4$ in water, and the liquid pH varied from 5 to 10. The setting times initial and final were determined with Gilmore needles. Teflon molds were used to prepare cement cylinders with a height of 12 mm and a diameter of 6 mm and soaking was carried out during 1 h, 24 h, 1, and 3 days in Ringer's solution at 37° C. prior to determination of the compressive strength. Scanning electron microscopy (SEM) was used for microstructural analysis. Finally, the samples were crushed using a mortar and pestle for X-ray powder diffraction analysis. Mercury porosimetry was used for porosity measurements.

Figure 2:
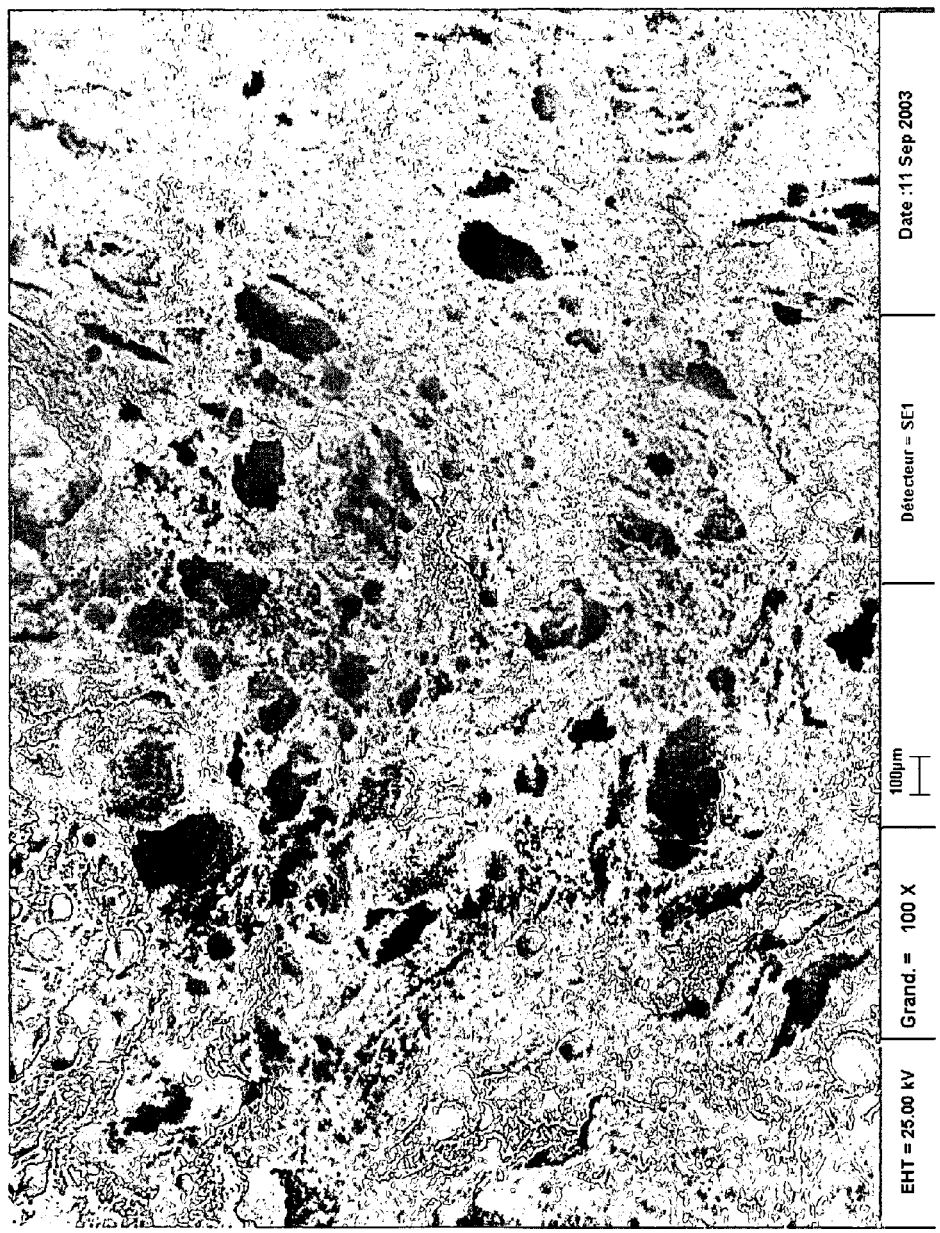
FIG. 2 shows an X-ray powder diffraction analysis of the sample of Example 2, 24 hrs after setting.
Figure 3:
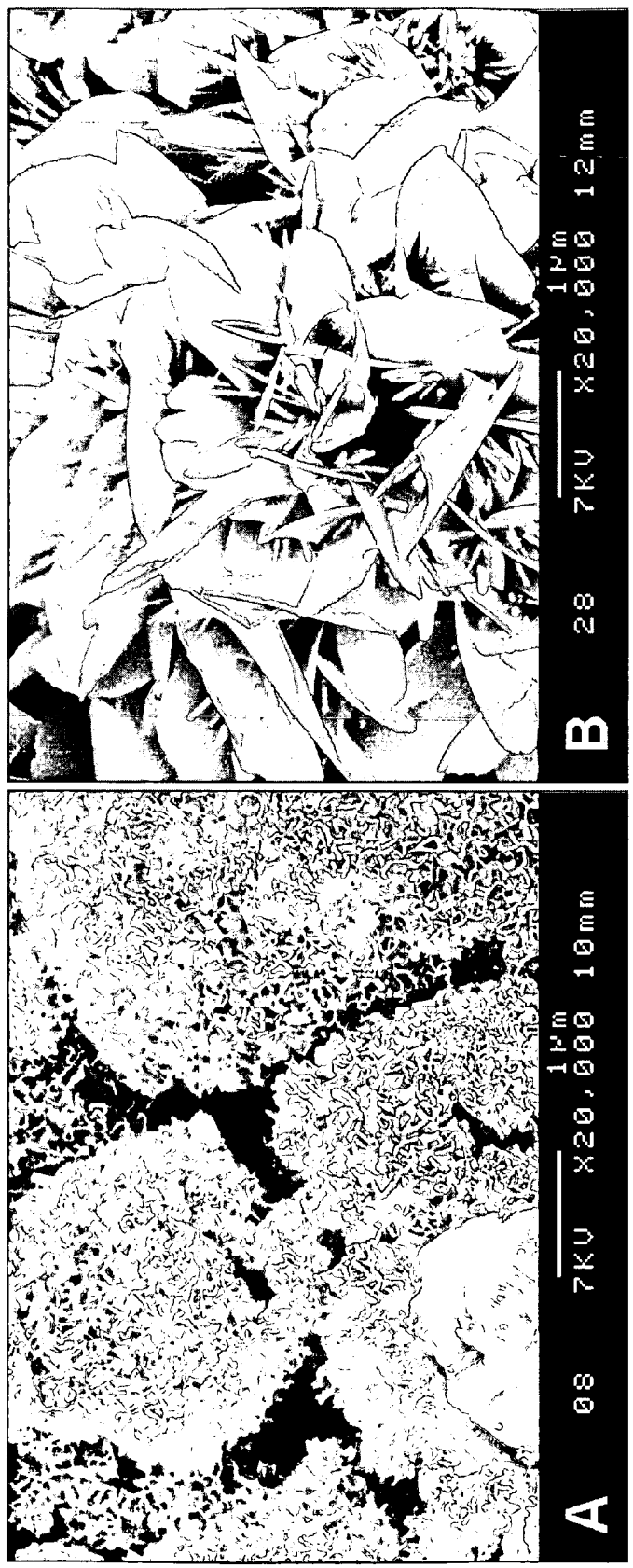
FIG. 3A shows the product of the reaction after 3 days setting.
FIG. 3B shows the product of the reaction with 100% alpha-TCP after 48 hours setting.
Figure 4:
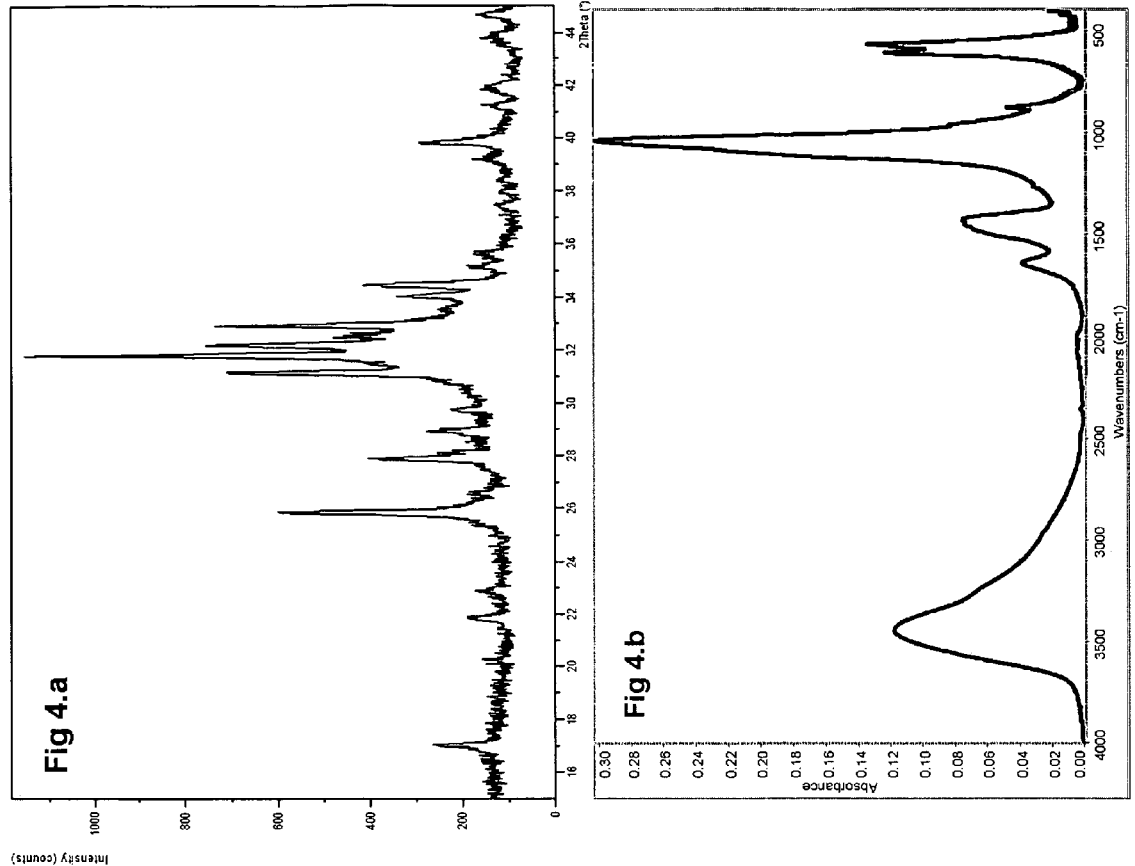
FIG. 4a is an X-ray diffraction profile illustrating the multiphasic composition of the cement 24 hours after setting.
FIG. 4b shows the conversion to mainly carbonatehydroxyapatite observed 48 hours after setting time.
Figure 5:
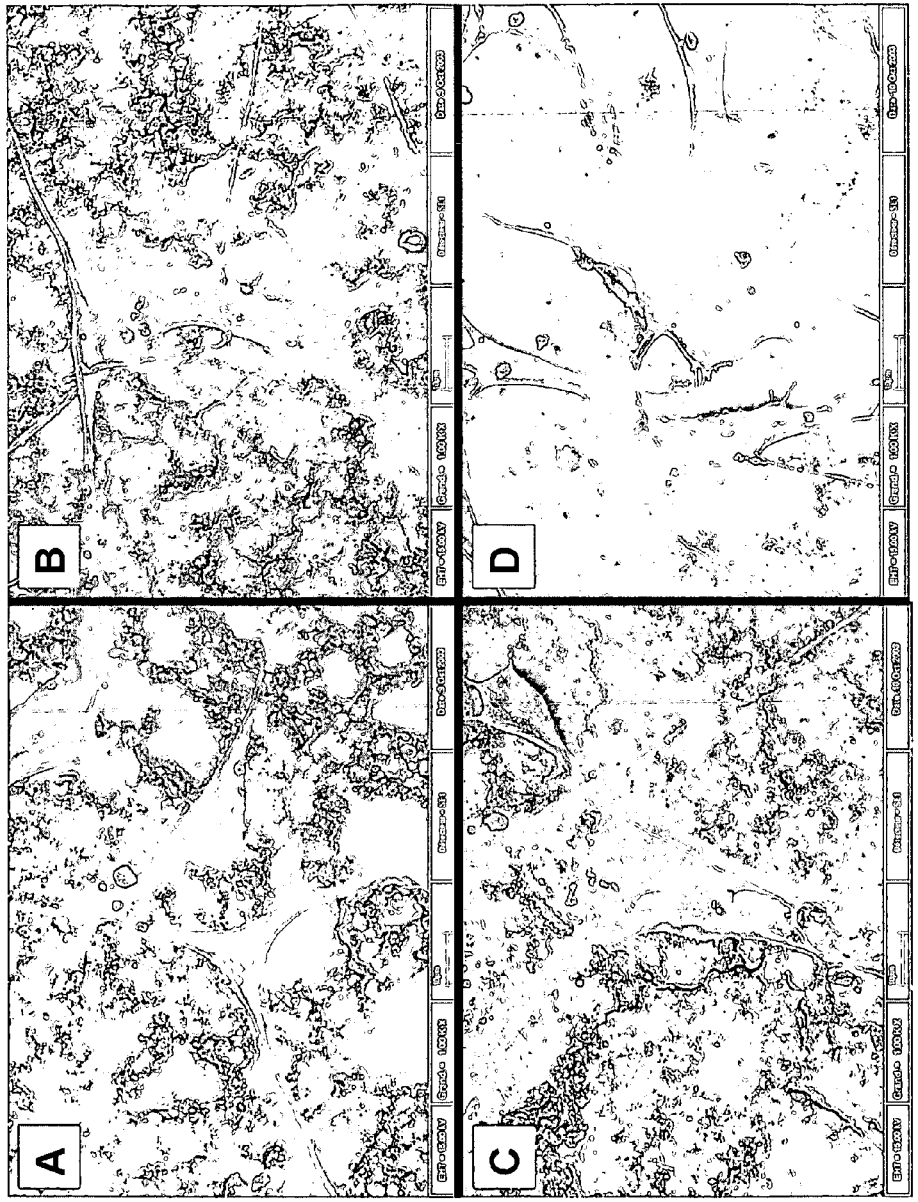
FIGS. 5A through 5D shows the results of SEM analysis on the discs of different cement formulations.

Presence of macroporosity is evident even 24 hrs after setting (FIG. 2). The end product of the reaction was poorly crystalline apatite of a formulation with composition described above and with liquid-to-powder ratio L/P=0.40 ml/g, liquid concentration, 3% $Na_2HPO_4$/$NaH_2PO_4$ in water and a pH of 6.5. Significant conversion of some of the calcium phosphate compounds in the powder component to apatite (shown by small cluster of crystals) was observed (FIG. 3A). In comparison, much larger apatite crystals were observed shown during the conversion of CPC consisting mainly of α-TCP (FIG. 3B). The multiphasic composition of the cement is still evident on the x-ray diffraction profile 24 hours after setting (FIG. 4a). Conversion to mainly carbonatehydroxyapatite is observed 48 hours after setting time (FIG. 4b).

EXAMPLE 3

In Vitro Cell Response to Cement Preparations

Eight formulations with different amorphous calcium phosphate were prepared to determine cell response.
Formulation A, α-TCP, ACCP-Zn, MCPA and CC
Formulation B, α-TCP, ACCP-Zn, MCPA and CC+BCP granules (40-200 microns)
Formulation C, α-TCP, ACCP-Mg, MCPA and CC+BCP granules (40-200 microns)
Formulation D, α-TCP, ACCP-F, MCPA and CC+BCP granules (40-200 microns)
(For all formulations, the BCP macroporous granules consisted of 60HA/40β-TCP).
Liquid-to-powder ratio L/P=0.40 ml/g; Liquid pH, 6.5; 1 hour and 24 hours after setting, the cements were soaked at 37° C. in Ringer's solution. Discs samples were prepared and sterilized using autoclave for 30 minutes at 121° C.

MC3T3-E1 cells, a non-transformed cell line established from newborn mouse calvarias, were used. MC3T3-E1 cells were grown in alpha MEM medium supplemented with 10% FCS, 1% penicillin/streptomycin and 1% L-Glutamine. Cells were subcultured once a week using Trypcin/EDTA and maintained at 37° C. in a humidified atmosphere of 5% $CO_2$ in air. Medium was completely renewed every two days. Cells were cultured onto discs of different cement samples in 24-multiwell plates at a final density of 10 000 cells/cm². Cells cultured in the absence of the materials were used as controls. After 15 days, media were removed and 100 ml of MTS solution was added in each well for 2-3 h. Colorimetric measurement of formazan dye was performed on a spectrophotomer with an OD reading at 490 nm. The discs were fixed with 4% glutaraldehyde in PBS (pH 7.2) for 1 h 30 at 4° C. after dehydration in graded alcohols, specimens were treated with graded mixture of ethanol/trichlorotrifluoroethane (75/25, 50/50, 25/75 and 0/100). They were then sputter-coated with gold-palladium and finally observed in scanning electron microscopy.

Cell morphology and proliferation. Results of SEM analysis showed that the cells on the discs of different cement formulations exhibited large spreading and cellular interconnections (FIGS. 5A through 5D).

Cell viability was measured as mitochondrial NADH/NADPH-dependent dehydrogenase activity, resulting in the cellular conversion of the tetrazolium salt MTS into a soluble formazan dye with the CellTiter 96 AqueousNon-radioactive cell proliferation assay. Results were expressed as relative MTS activity compared to control conditions (cells cultured in the absence of the cement discs). Results showed that cell viability in the presence of the cement discs were not statistically different from that in control (FIG. 6).

EXAMPLE 4

Animal Experiments

Cement samples were prepared by mixing sterilized powder and liquid. Two compositions were tested. The cement compositions were (a) 45% α-TCP, 15% ACCP, 30% BCP granules (40-200 microns), 5% MCPA and 5% CC and (b) 45% α-TCP, 15% ACCP-F, 30% BCP granules (40-200 microns), 5% MCPA and 5% CC. Liquid-to-powder ratio L/P=0.40 ml/g; Liquid at pH 6.5 were used for both compositions. The cement pastes were injected into the surgically created bone defect (3 mm diameter) in rat femora. Implantations were performed bilaterally on six rats in aseptic conditions and under general anaesthesia. The first three rats were sacrificed after 2 weeks. The second three rats were sacrificed after 3 weeks. Results showed no difference between 2 and 3 weeks and the cement matrix partially dissolved forming an open structure and interconnective porosity (FIG. 7). New bone was observed directly in contact with the BCP granules (FIG. 7).

While the present invention has been described in terms of specific embodiments thereof, it will be understood in view of the present disclosure, that numerous variations upon the invention are now enabled to those skilled in the art, which variations yet reside within the scope of the present teaching. Accordingly, the invention is to be broadly construed, and limited only by the scope and spirit of the claims now appended hereto.

The invention claimed is:

1. A self-setting calcium phosphate cement composition comprising a mixture of a powder and an aqueous solution which results in the formation of a poorly crystalline apatite similar to bone apatite as the end product of the self-setting; the said powder phase comprising calcium phosphate compounds of differing rates of resorbability, a fraction of said powder phase comprising α-TCP or TTCP, macroporous biphasic calcium phosphate (BCP) granules consisting of a mixture of HA and β-TCP, and ACP or stabilized ACP; and a fraction of 1-10 wt% of said powder phase comprising one or more members selected from the group consisting of monocalcum phosphate, monocalcium phosphate monohydrate, calcium carbonate, and ACCP.

2. A composition in accordance with claim 1, wherein the aqueous solution of the cement composition comprises a sodium phosphate solution with pH ranging from 5 to 10.

3. A composition in accordance with claim 1, wherein the w/w ratio of the BCP granules to the remaining calcium phosphate compounds is selected such that the final result of their combination does not change the final pH of the mixture of the powder and liquid components.

4. A composition in accordance with claim 3, wherein the calcium phosphate granules comprises 10 to 70% by weight of the total powder components.

5. A composition in accordance with claim 1, wherein the majority of the weight of said calcium phosphate compounds is provided by α-tricalcium phosphate.

6. A composition in accordance with claim 1, wherein the majority of the weight of said calcium phosphate compounds is provided by tetracalcium phosphate.

7. A composition in accordance with claim 1, wherein the majority of the weight of said calcium phosphate compounds comprises α-tricalcium phosphate and/or tetracalcium phosphate.

8. A composition in accordance with claim 1, wherein said amorphous calcium phosphate is stabilized by one or more ions selected from the group consisting of carbonate, magnesium, zinc, fluoride, and pyrophosphate ions.

9. A composition in accordance with claim 1, wherein said calcium phosphate granules have a particle size between about 40 microns and 600 microns.

10. A composition in accordance with claim 1, wherein the percentage (% w/w) of the combination of the calcium phosphate compounds excluding BCP is from 10% to 70% based on the total dry weight of the powder phase.

11. A composition in accordance with claim 1, wherein the content (% w/w) of said unstabilized or stabilized amorphous calcium phosphate, is from 5% to 30% based on the total dry weight of the powder phase.

12. A composition in accordance with claim 1, wherein the content (% w/w) of the calcium phosphate granules is from 10% to 70% based on the total dry weight of the powder phase.

13. A composition in accordance with claim 2, characterized in that the cement liquid comprises sodium orthophosphate or potassium orthophosphate.

14. A composition in accordance with claim 2, wherein said aqueous solution has a pH below 7.

15. A composition in accordance with claim 2, additionally comprising a biodegradable polymer as an additive to control the cement consistency and increase injectability.

16. A composition in accordance with claim 3, wherein the cement mixture further includes one or more agents selected from the group consisting of a pharmaceutically active ingredient and a growth factor.

17. A composition in accordance with claim 3, wherein the said growth factor is a bone morphogenic protein or a fibroblast growth factor.

18. A composition in accordance with claim 3, wherein the mixture further comprises calcium sulfate hemihydrate, and/or calcium sulfate dehydrate.

19. A composition in accordance with claim 3, wherein the measurable pH value of the cement paste during setting is about 6.5.

* * * * *